US00PP31796P3

(12) United States Plant Patent
Hughes

(10) Patent No.: US PP31,796 P3
(45) Date of Patent: May 26, 2020

(54) ***LEUCOTHOE* PLANT NAMED 'BLULE1801'**

(50) Latin Name: *Leucothoe fontanesiana*
Varietal Denomination: BLULE1801

(71) Applicant: Blue Mountain Nurseries, Ltd., Tapanui (NZ)

(72) Inventor: Chris Hughes, Tapanui (NZ)

(73) Assignee: Blue Mountain Nurseries, Ltd., Tapanui (NZ)

( * ) Notice: Subject to any disclaimer, the term of this patent is extended or adjusted under 35 U.S.C. 154(b) by 0 days.

(21) Appl. No.: 16/501,542

(22) Filed: Apr. 26, 2019

(65) Prior Publication Data

US 2020/0084933 P1 Mar. 12, 2020

(30) Foreign Application Priority Data

Sep. 11, 2018 (NZ) ..... PBR 2018/2345

(51) Int. Cl.
*A01H 5/00* (2018.01)

(52) U.S. Cl.
USPC ..... Plt./226

(58) Field of Classification Search
USPC ..... Plt./226
CPC ... A01H 5/00; A01H 5/02; A01H 5/12; A01H 6/36
See application file for complete search history.

*Primary Examiner* — June Hwu
(74) *Attorney, Agent, or Firm* — Samuel R. McCoy, Jr.

(57) ABSTRACT

A new and distinct variety of *Leucothoe* plant named 'BLULE1801' which is characterized by the combination of a compact growth habit, juvenile foliage that is suffused with a red coloration, dark green mature foliage which becomes progressively suffused with a deep maroon in cool weather, and the stability of all characteristics from generation to generation.

3 Drawing Sheets

Latin name of the genus and species: The Latin name of the genus and species of the novel variety disclosed herein is *Leucothoe fontanesiana.*

Variety denomination: The inventive variety of *Leucothoe* disclosed herein has been given the variety denomination 'BLULE1801'.

CROSS REFERENCE TO RELATED APPLICATIONS

This application claims priority to the Community Plant Variety Rights application number 2018/2345 filed Sep. 11, 2018, which is herein incorporated by reference.

BACKGROUND OF THE INVENTION

Parentage: 'BLULE1801' is a seedling selection which resulted from the open pollination of a plurality of cultivated unnamed *Leucothoe fontanesiana* plants (not patented) in the year 1980. All plants, and therefore all potential parents of the instant plant, shared the exemplary phenotype of the species. In 1985, the inventor discovered a seedling from the cross of 1980 at his commercial plant nursery in Tapanui, New Zealand. The seedling was noted for its compact habit and unique foliage characteristics and was subsequently isolated for further evaluation in order to confirm the distinctness and stability of the characteristics first observed. After further evaluation it was determined that the unique characteristics of the candidate plant would prove favorable for commercial marketability. The new variety was given the breeder denomination 'BLULE1801'.

Asexual Reproduction: Asexual reproduction of 'BLULE1801', by way of stem cuttings, was first initiated in or around the year 2000 at the inventor's commercial greenhouse in Tapanui, New Zealand. Through ten subsequent generations, the unique features of this cultivar have proven to be stable and true to type.

SUMMARY OF THE INVENTION

The cultivar 'BLULE1801' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'BLULE1801'. These characteristics in combination distinguish 'BLULE1801' as a new and distinct *Leucothoe* cultivar:

1. *Leucothoe* 'BLULE1801' exhibits a compact, flattened globular growth habit; and
2. *Leucothoe* 'BLULE1801' exhibits newly emerged foliage which is suffused with a red coloration; and
3. *Leucothoe* 'BLULE1801' exhibits green mature foliage which becomes progressively suffused with a deep maroon coloration as temperature decreases in autumn and winter.

BOTANICAL DESCRIPTION OF THE PLANT

Figure 1:
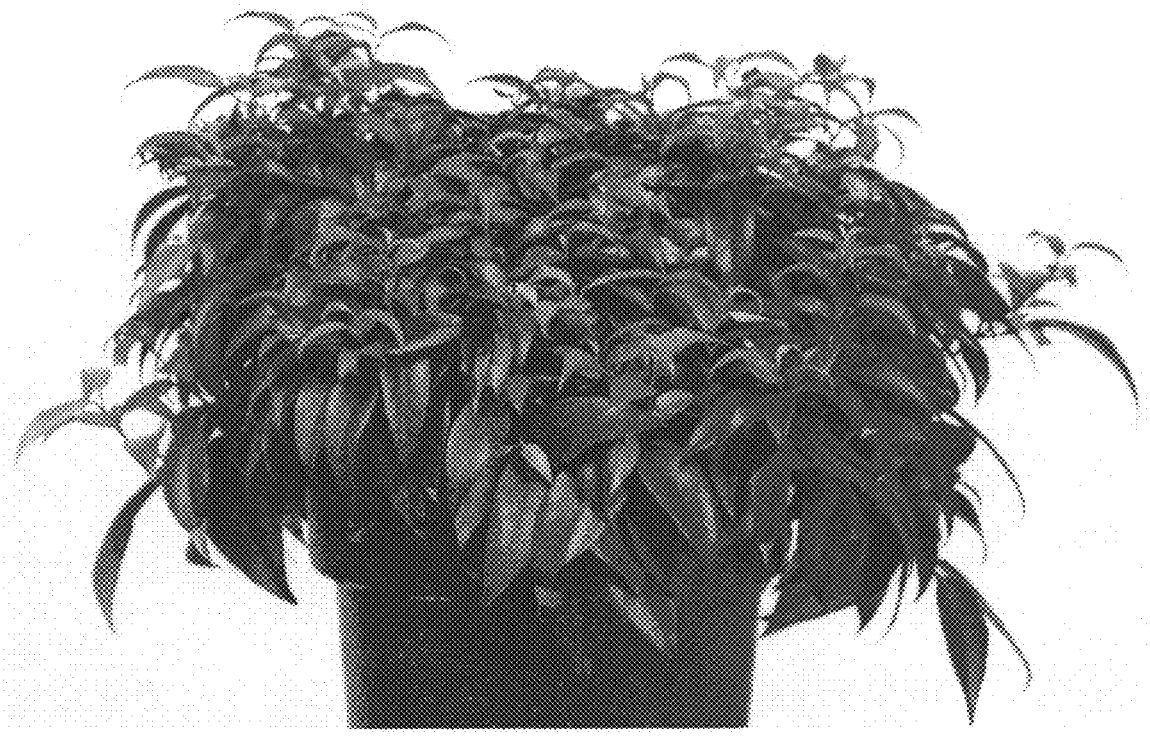
FIG. 1 illustrates, as nearly true as it is reasonably possible to make the same in color photographs of this type, an exemplary plant of 'BLULE1801' grown in a grown in a commercial greenhouse in Tapanui, New Zealand. This plant is approximately 21 months old, shown planted in a 21 cm container.
Figure 2:
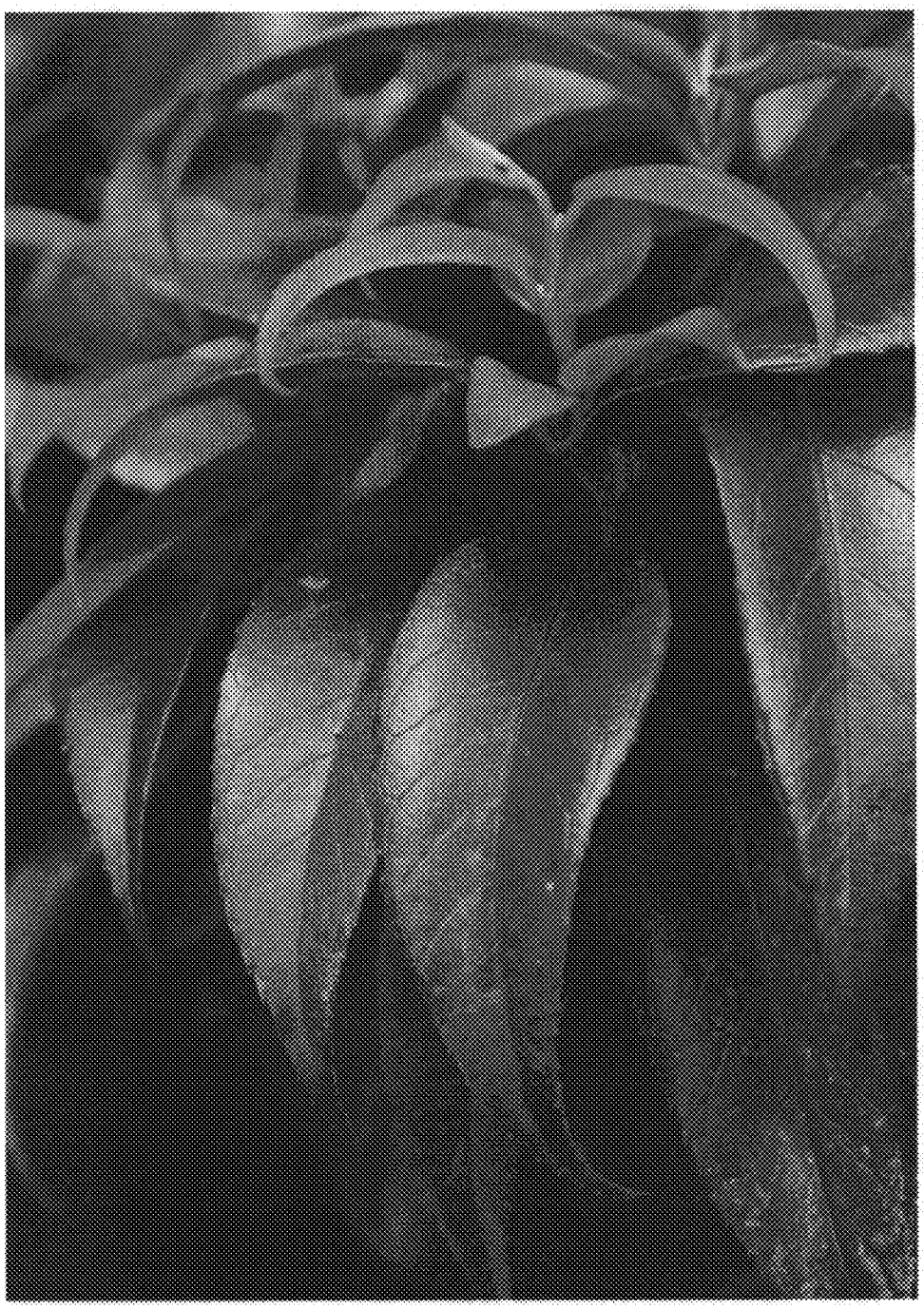
FIG. 2 illustrates, as nearly true as it is reasonably possible to make the same in color photographs of this type, the typical coloration of the mature foliage of 'BLULE1801', grown in a commercial greenhouse in Tapanui, New Zealand.
Figure 3:
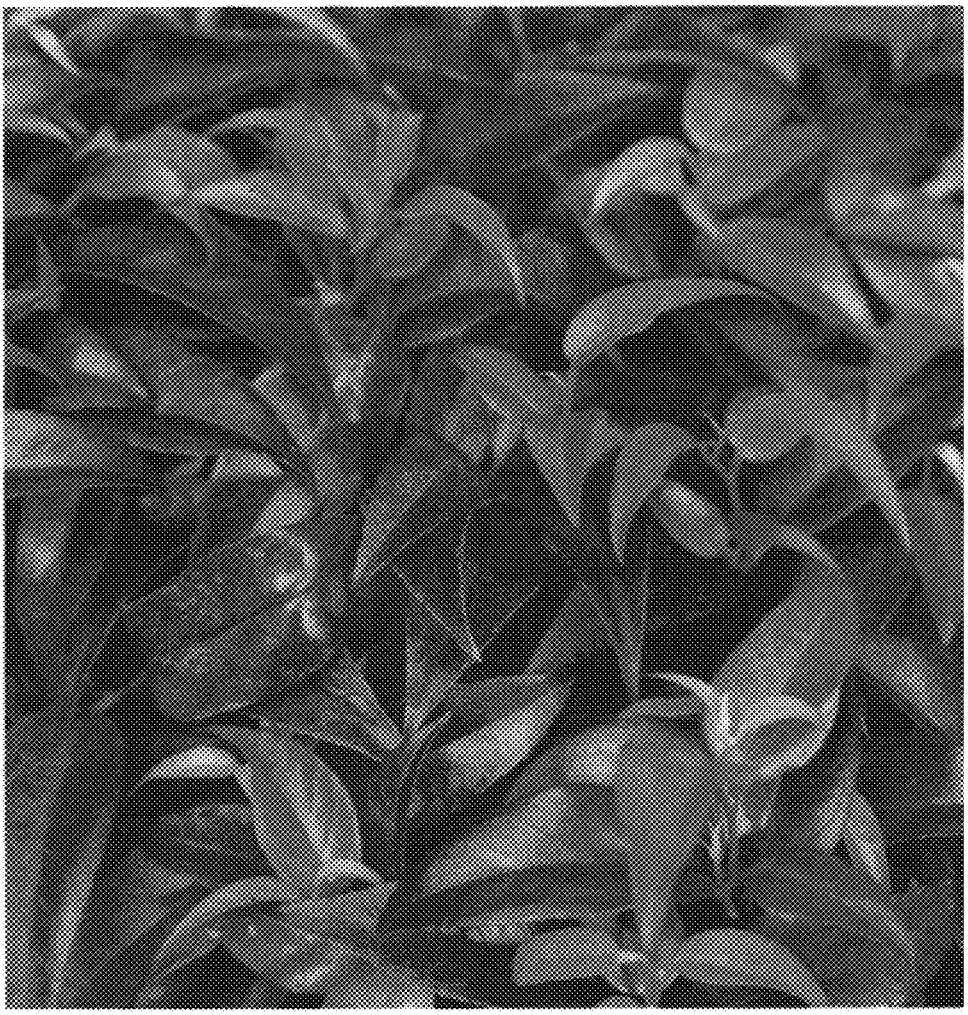
FIG. 3 illustrates, as nearly true as it is reasonably possible to make the same in color photographs of this type, the typical autumn coloration of the juvenile and mature foliage of 'BLULE1801'.

The following observations and measurements were made in September of 2018 and describe a sample set of six 21 month-old 'BLULE1801' plants grown in 21 cm nursery pots at a plant nursery in Tapanui, New Zealand. Plants were produced outdoors, in full sun, using conventional production protocols for *Leucothoe* which consisted of drip irrigation and no fertilizer applications. No pest or disease control measures were utilized in production.

Those skilled in the art will appreciate that certain characteristics will vary with older or, conversely, with younger plants. 'BLULE1801' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2015 (sixth edition).

A botanical description of 'BLULE1801' and comparisons with the parent plants and most similar commercial variety of *Leucothoe* are provided below.

Plant description:

*Growth habit.*—Compact; broad spreading to spreading-upright woody perennial.

*Plant form.*—Irregular flattened globular.

*Average height.*—23.4 cm from the soil level to the top of the foliar plane.

*Plant spread.*—Average of 46.6 cm.

*Growth rate.*—Moderately fast.

*Plant vigor.*—Moderately to highly vigorous.

*Propagation type.*—Stem cuttings.

*Time to produce a rooted cutting.*—Approximately 112 days to produce a rooted cutting at approximately 18 degrees Celsius.

*Time to produce a finished plant.*—32 months.

*Disease resistance.*—Neither resistance nor susceptibility to typical *Leucothoe* pests and diseases has been observed.

*Environmental tolerances.*—Adapt to, at least, USDA Zones 6 through 10 and temperatures as high as 40 degrees Celsius; moderate tolerance to rain; moderate to high tolerance to wind.

Root system:

*General.*—Dense and very freely branched rooting; roots are slightly fibrous.

*Distribution in the soil profile.*—Shallow to moderately deep.

*Diameter of roots.*—0.1 cm on average.

*Texture.*—Smooth; no root hairs.

*Color.*—Greyed-orange, nearest to RHS 164A.

Stem:

*General branching habit.*—Basally branching main stems; freely branching with lateral branches. Pinching isn't required but will improve branching.

*Quantity of main stems per plant.*—30.

*Quantity of lateral branches.*—60.

*Length of lateral branches.*—Approximately 9.2 cm.

*Diameter of lateral branches.*—Approximately 0.2 cm.

*Internode length.*—Approximately 1.1 cm.

*Attitude.*—At an average angle of 40 degrees to vertical.

*Cross-section.*—Rounded.

*Aspect.*—Flexuous.

*Texture.*—Densely covered with very short glandular hairs which are 0.1 mm long, on average.

*Luster.*—Matte.

*Strength.*—Strong.

*Color, juvenile.*—Greyed-purple, nearest to RHS 184A.

*Color, mature.*—Yellow-green, nearest to a mixture of RHS 144A and 144B.

*Color at internodes.*—Yellow-green, nearest to a mixture of RHS 144A and 144B.

*Color of the oldest wood.*—Greyed-brown, nearest to a mixture of RHS N199C and N199D.

Foliage:

*Arrangement.*—Alternate; distichous.

*Division.*—Simple.

*Quantity.*—9 leaves per lateral branch.

*Attitude.*—Upward.

*Lamina.*—Shape — Narrow ovate. Aspect — Slightly convex, slightly revolute, and slightly carinate. Dimensions — 8.4 cm long and 3.2 cm wide. Thickness — Approximately 0.5 cm. Apex — Long and narrowly apiculate. Base — Obtuse. Margin — Serrate and slightly revolute. Texture of top surface — Smooth, glabrous, and glossy. Texture of bottom surface — Smooth, glabrous, and matte to very slightly glossy. Color — Juvenile foliage, adaxial surface — Yellow-green, nearest to RHS 144B. In autumn, juvenile foliage becomes heavily suffused with greyed-red, in between RHS 183A and 185A. Juvenile foliage, abaxial surface — Yellow-green, nearest to RHS 146D. In autumn, juvenile foliage becomes heavily suffused with greyed-red, RHS 182B. Mature foliage, adaxial surface — Nearest to a mixture of green and yellow-green, RHS NN137A and 147A. In autumn, foliage becomes heavily suffused with a mixture of greyed-purple and brown, nearest to RHS N186C and 200A. Mature foliage, abaxial surface — Yellow-green, nearest to a mixture of RHS 146B and 147B. In autumn, foliage becomes heavily suffused with yellow-green, in between RHS 146C and 147C. Venation — Pattern — Pinnate. Color, adaxial surface — Yellow-green, nearest to RHS 152B. Color, adaxial surface — Yellow-green, nearest to a mixture of RHS 144B and 144C.

*Petiole.*—Length — 0.6 cm. Diameter — 0.2 cm. Strength — Strong. Texture — Densely covered with very short glandular hairs which are 0.1 mm long, on average. Luster — Matte. Color, adaxial surface — Yellow-green, nearest to RHS 146C, and suffused with greyed-red, nearest to a mixture of RHS 181A and 181B. Color, abaxial surface — Yellow-green, nearest to a mixture of RHS 144C and 146D, and suffused with greyed-red, nearest to a mixture of RHS 181A and 181B.

Inflorescence: No flowering has been observed to date.

Comparison with the parent plant:

Plants of the new cultivar 'BLULE1801' differ from the parents, unnamed *Leucothoe fontanesiana* plants (not patented) with the phenotype of the species, in the following characteristics described in Table 1 below.

TABLE 1

| Characteristic | 'BLULE1801' | The parents. |
|---|---|---|
| Growth habit. | Compact; globular. | Less compact; open, arching. |
| Overall plant height. | Up to 50 cm. | Up to 150 cm. |
| Leaf shape. | Narrow ovate. | Lanceolate. |
| General coloration of the foliage. | Dark green and heavily suffused with deep burgundy in autumn. | Dark green and lightly to moderately suffused with red in autumn. |

Comparison with the closest known comparator: Plants of the new cultivar 'BLULE1801' differs from the commercial variety, *Leucothoe* 'Rainbow' (not patented) in the following characteristics described in Table 2 below.

TABLE 2

| Characteristic | 'BLULE1801' | 'Rainbow' |
|---|---|---|
| Growth habit. | More compact. | Less compact. |
| General coloration of the foliage. | Dark green and heavily suffused with deep burgundy in autumn. | Light green and cream variegation and lightly suffused with red. |

That which is claimed is:

1. A new and distinct variety of *Leucothoe* plant named 'BLULE1801', substantially as described and illustrated herein.

* * * * *